United States Patent [19]

Kieturakis

[11] Patent Number: 5,603,720
[45] Date of Patent: Feb. 18, 1997

[54] SURGICAL METHOD FOR USE WITH TRANSLUMINAL DILATION CATHETER

[76] Inventor: Maciej J. Kieturakis, 372 Beverly Dr., San Carlos, Calif. 94070

[21] Appl. No.: 380,674

[22] Filed: Jan. 27, 1995

[51] Int. Cl.⁶ ........................................ A61B 17/32
[52] U.S. Cl. ...................... 606/191; 606/194; 128/898; 128/899
[58] Field of Search ............................. 606/191, 192, 606/194, 195, 198, 159; 623/1, 12; 128/898, 899

[56] References Cited

U.S. PATENT DOCUMENTS

| | | | |
|---|---|---|---|
| 4,315,511 | 2/1982 | Chin | 606/159 |
| 5,282,484 | 2/1994 | Reger | 606/159 |
| 5,356,418 | 10/1994 | Shturman | 606/159 |
| 5,415,634 | 5/1995 | Glynn et al. | 606/192 |

*Primary Examiner*—Michael Powell Buiz
*Assistant Examiner*—Mark S. Leonardo
*Attorney, Agent, or Firm*—Skjerven, Morrill, MacPherson, Franklin & Friel; Norman R. Klivans

[57] ABSTRACT

A surgical device for facilitating an intraluminal treatment of a stenosis in an anatomic vessel. The device comprises a spirally-configured constraint defining a spiral gap between convolutions that cooperates with a longitudinally-extending interior bore dimensioned to receive an anatomic vessel, for example an artery. The artery is disposed with the interior bore by "corkscrewing" the constraint around the exterior of the vessel, thus constraining the artery's transverse dimension. In performing an exemplary method of the invention, the surgeon captures the artery in constraint's interior bore and then widens the stenosis with a balloon catheter. The constraint allows the use of relatively high fluid pressures in the balloon catheter to compact occlusions in the stenosed vessel against the extraluminal constraint while at the same time limiting radial expansion of vessel walls to prevent over-expansion or perforation of the vessel.

9 Claims, 4 Drawing Sheets

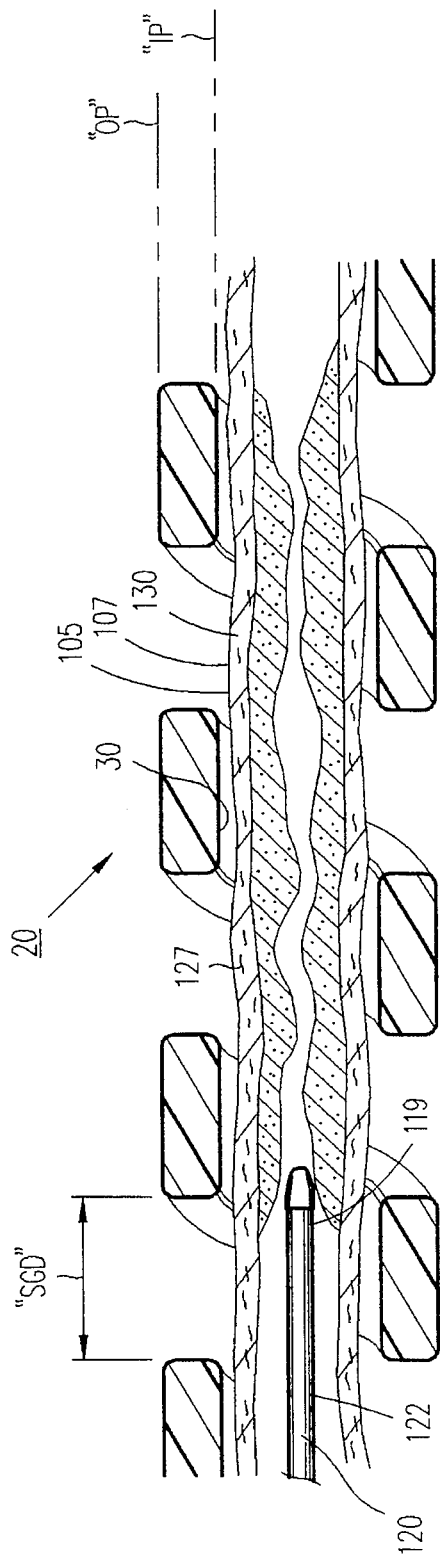
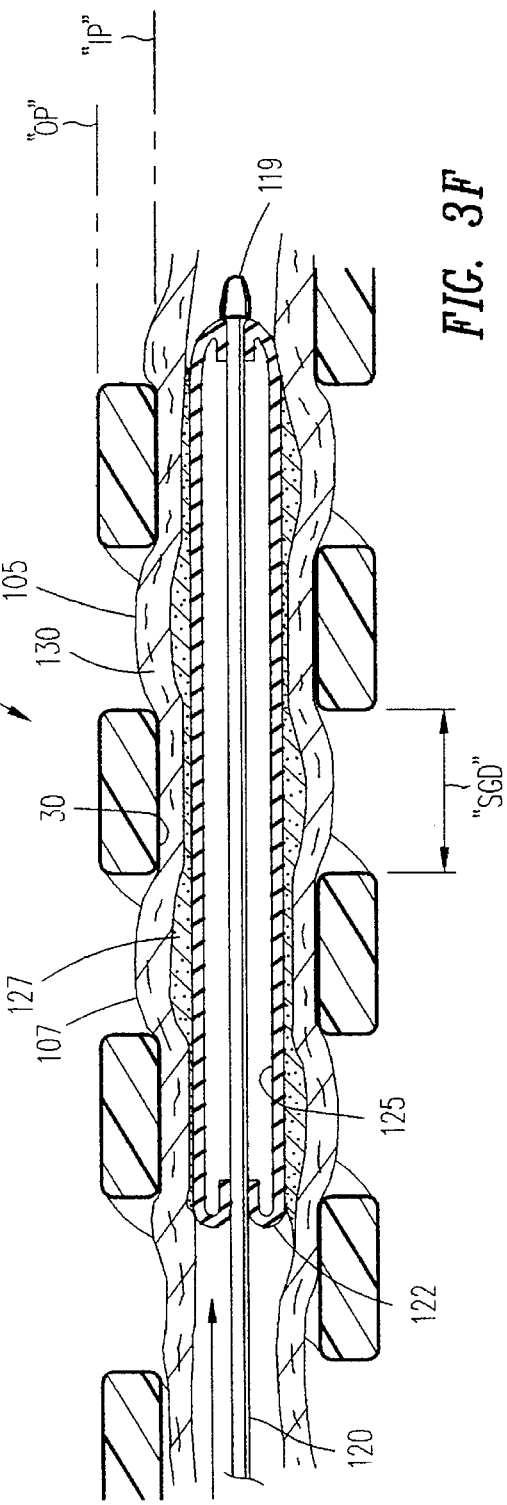

SURGICAL METHOD FOR USE WITH TRANSLUMINAL DILATION CATHETER

CROSS-REFERENCE TO RELATED APPLICATIONS

This application is related to the following co-pending and commonly invented U.S. Patent applications, which are incorporated herein by reference: Ser. No. 08/367,755, filed Dec. 31, 1994, now Pat. No. 5,505,297; Ser. No. 08/287,580, filed Aug. 9, 1994, allowed.

BACKGROUND OF THE INVENTION

1. Field of the Invention

This invention relates to surgical instrumentation and more particularly to a device and method of use for facilitating treatment of a stenosis in an anatomic lumen, for example, a stenosed region of a blood vessel.

2. Description of Prior Art

Various types of endovascular catheters are utilized to maneuver through a patient's arteriovenous system to treat a stenosis in a particular location. Such treatments include dilation of the stenosis with a dilation-type catheter or so-called balloon catheter. A balloon catheter, when inflated with a pressurized fluid, will distend and increase in transverse dimension in order to widen a stenosis. An occlusion in an blood vessel may be compacted or compressed as the stenosis is widened. A balloon-type catheter typically is inflated to a certain transverse dimension at a predetermined maximum pressure level to insure against over-expansion. Should the balloon over-expand, for example in a critical artery, the balloon could perforate the vessel wall resulting in serious injury to the patient.

SUMMARY OF THE INVENTION

The device of the present invention is adapted for treatment of a stenosis in an anatomic vessel and is described with reference to an improved method of treating an hourglass stenosis of an external iliac artery with a dilation-type catheter, although the instrument and method may be used in many other procedures.

In general, the extraluminal constraint comprises a vessel-constraining structure adapted for placement around an exterior of a vessel wall surrounding a stenosed region. The preferred embodiment of the extraluminal constraint is a spiral member defining a spiral gap between convolutions and further defining a longitudinally-extending interior bore dimensioned to receive the blood vessel. The spiral gap is dimensioned to cooperate with a similar interior bore dimension, thus allowing a blood vessel to disposed within the bore "corkscrewing" the constraint around the exterior of the blood vessel.

In performing the exemplary method of the present invention with reference to the stenosis of the external iliac artery, the surgeon makes an incision in the patient's groin to expose the femoral artery. Typically, the surgeon then advances an intraluminal guide into the artery to serve as a guide for the spiral constraint, as such method is disclosed in Ser. No. 08/367,755, filed Dec. 31, 1994, now U.S. Pat. No. 5,505,297. The distal end of the constraint's spiral gap is placed around the artery exposed in the incision. The surgeon then rotates the extraluminal constraint and captures the artery in constraint's interior bore thus constraining the artery's transverse dimension against over-expansion. Thereafter, the surgeon withdraws the guide probe and introduces a balloon catheter into the artery and advances its distal working end to the stenosed region then surrounded by the spiral constraint. An inflation medium is introduced into the catheter thereby expanding the balloon walls and compressing the occlusion against the constraint. The use of the constraint allows the use of relatively high fluid pressures in the balloon to compact the occlusion, as compared to a conventional balloon dilation procedure. At the same time, the constraint limits radial expansion of vessel walls and protects against over-expansion or perforation of the artery walls.

In general, the extraluminal constraint of the present invention advantageously provides a device and method for preventing over-expansion of a blood vessel caused by an endovascular therapy by constraining the vessel walls in the interior bore of the constraint.

The present invention also provides a method that allows a dilation-type catheter to compact an occlusion in a vessel against interior bore surfaces of the constraint. The extraluminal constraint also provides a device and method that allows a dilation catheter to utilize relatively high fluid pressures to compact an occlusion in a vessel.

The extraluminal constraint of the present invention advantageously provides a method that allows an atherectomy-type catheter to effectively cut an occlusion in a vessel by applying radial inward pressure on the vessel to press the occlusion against the cutter of the atherectomy catheter.

The present invention advantageously provides an extraluminal constraint having radiopaque marks for viewing with imaging technologies.

The present invention provides instruments that are inexpensive and may be disposable. Additional advantages and features of the present invention will appear in the following description.

BRIEF DESCRIPTION OF THE DRAWINGS

FIGS. 3A–3F are illustrations showing the manner in which the instrument of FIG. 1 is utilized to perform a method of the present invention; FIGS. 3A–3B being cartoons of a patient's body, FIGS. 3C–3D being elevational views of an artery, and FIGS. 3E–3F being enlarged partial sectional views of an occluded region of the artery.

DESCRIPTION OF THE INVENTION

Figure 1:
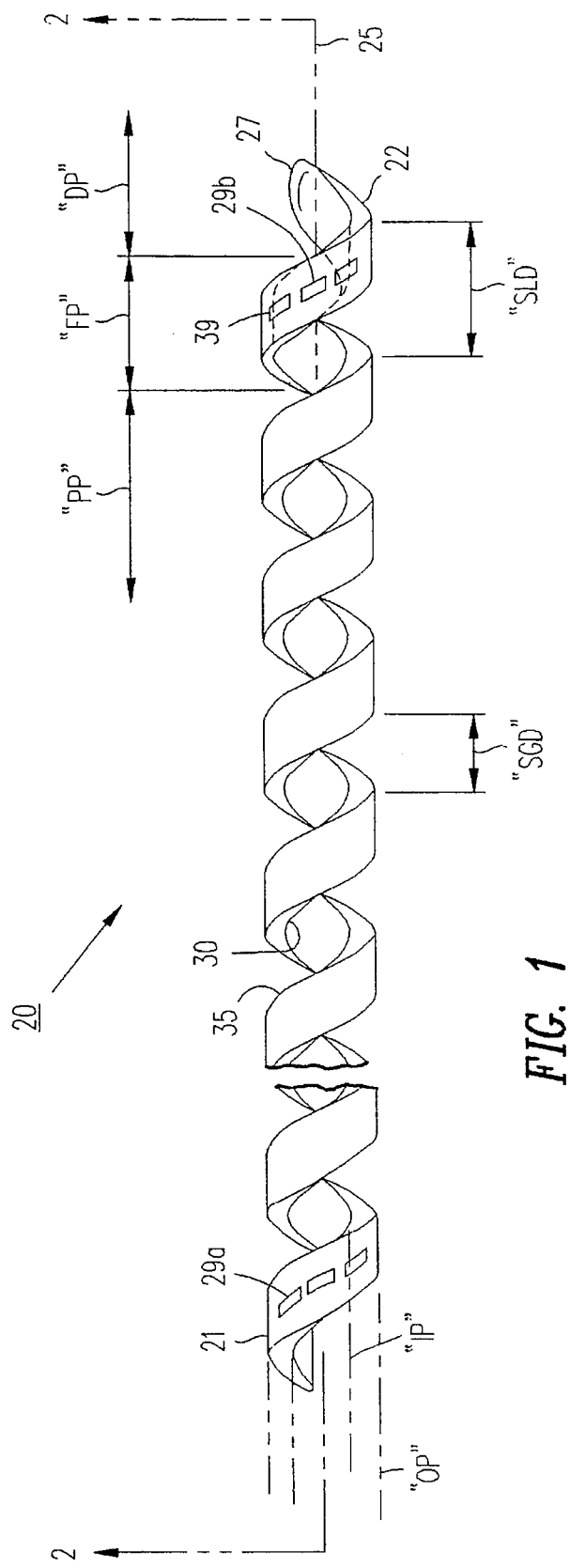
FIG. 1 is an elevational view of an extraluminal constraint of the present invention.
Figure 2:
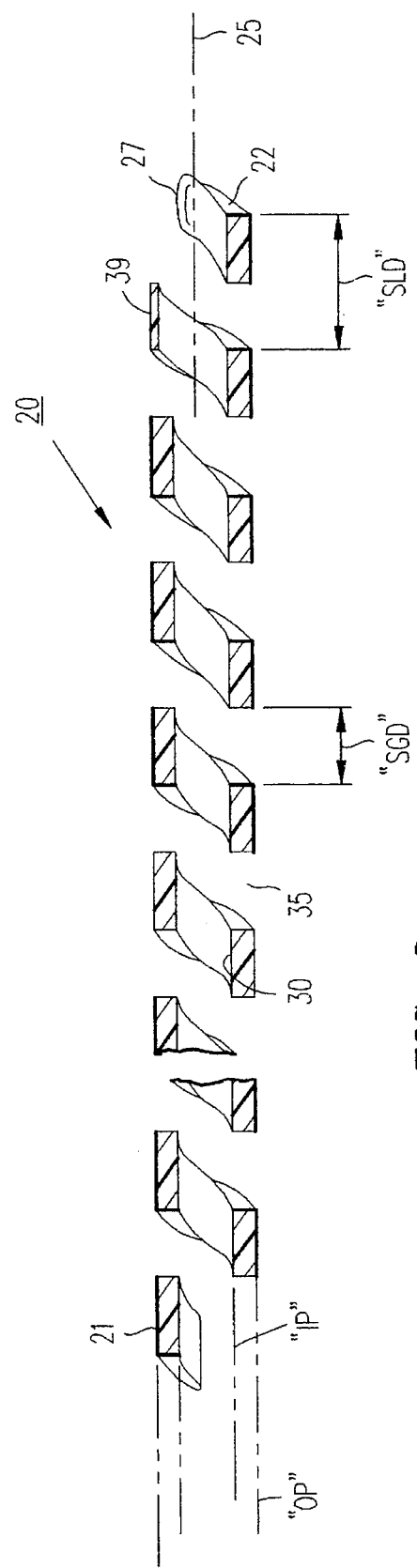
FIG. 2 is a longitudinal sectional view of the device of FIG. 1 taken along line 2—2 of FIG. 1 rotated 90°.

By way of example, FIGS. 1–2 illustrate extraluminal constraint 20 adapted for constraint of an external iliac artery that comprises a spiral element with proximal and distal ends, 21 and 22, extending around axis 25. Constraint or spiral member 20 includes distal tip 27 that is blunt or rounded and the member is made of any suitable material such as a slightly flexible medical grade plastic. As shown in FIG. 1, radiopaque marks 29a and 29b are placed at the proximal and distal ends of the device for imaging during use of the constraint. It should be appreciated that the entire constraint may be made of radiopaque material for imaging purposes.

Spiral member 20 for an iliac artery procedure has a cylindrical-shaped outer periphery "OP" having a diameter of approximately 10 mm. to 30 mm. with a overall length ranging from 200 mm. to 400 mm. Referring to FIG. 1, bore 30 along axis 25 is defined by the constraint's inner periphery "IP" for accommodating an iliac artery and may be manufactured with various diameters ranging from 5 mm. to 15 mm. for various patients (all dimensions not limiting).

Spiral member 20 defines a spiral lead dimension "SLD" as shown in FIG. 1 which may range from 5 mm. to 100 mm. (not limiting). Spiral lead dimension "SLD" may be defined as the axial travel resulting from an angular movement of 360° of a line extending from axis 25 outwardly as the line passes through a helix around axis 25, and as such, spiral lead dimension "SLD" equals the distance between like portions of each convolution. As shown in FIG. 1, spiral member 20 further defines spiral gap 35 between adjacent convolutions. Spiral gap 35 defines a spiral gap dimension "SGD" as shown in FIG. 1 which generally is constant and may range from 4 mm. to 20 mm. (not limiting). The spiral gap dimension "SGD" generally is similar to the diameter of bore 30 for reasons explained below.

FIGS. 1–2 depict flexible portion "FP" of spiral member 20 wherein a reduced cross-section portion 39 (see FIG. 2) of the spiral member allows distal portion "DP" to flex more easily along axis 25 relative to proximal portion "PP" for reasons explained below. The radial dimension "RD" across a single convolution of spiral member 20 is a suitably thick dimension to resist torsional forces as described below.

The use of constraint 20 in performing a method of the present invention now may be described briefly in balloon dilation of an hour-glass stenosis of an external iliac artery as shown in cartoons (FIGS. 3A–3B) and plan and sectional views (FIGS. 3C–3F).

Figure 3B:
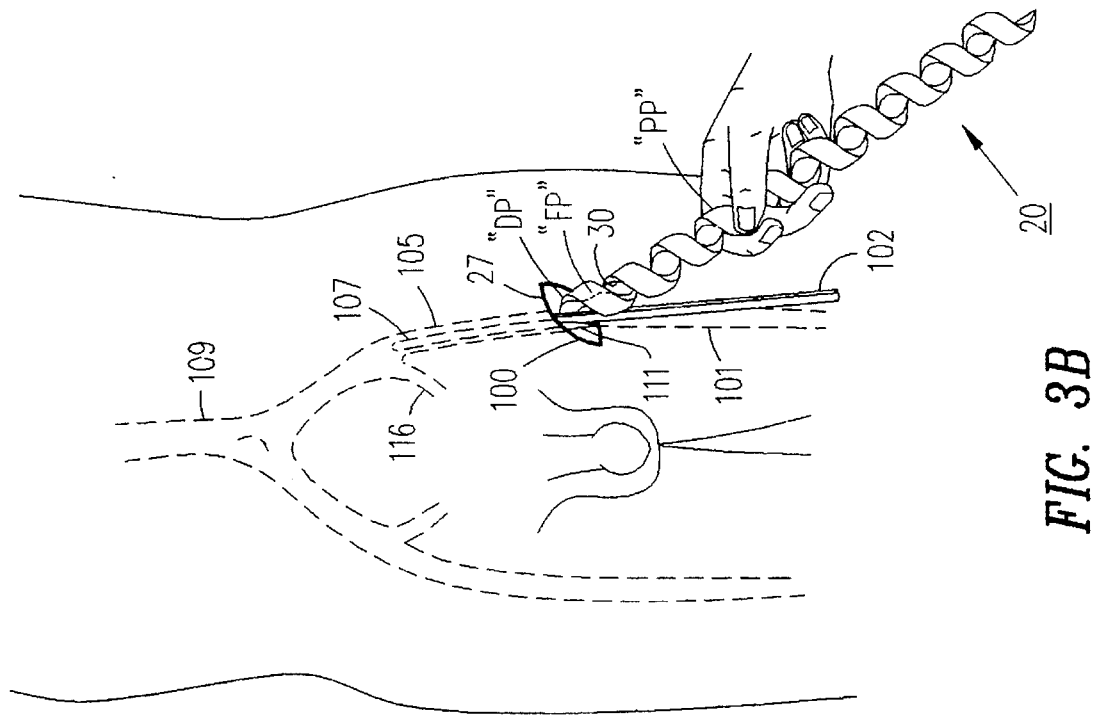
Figure 3A:
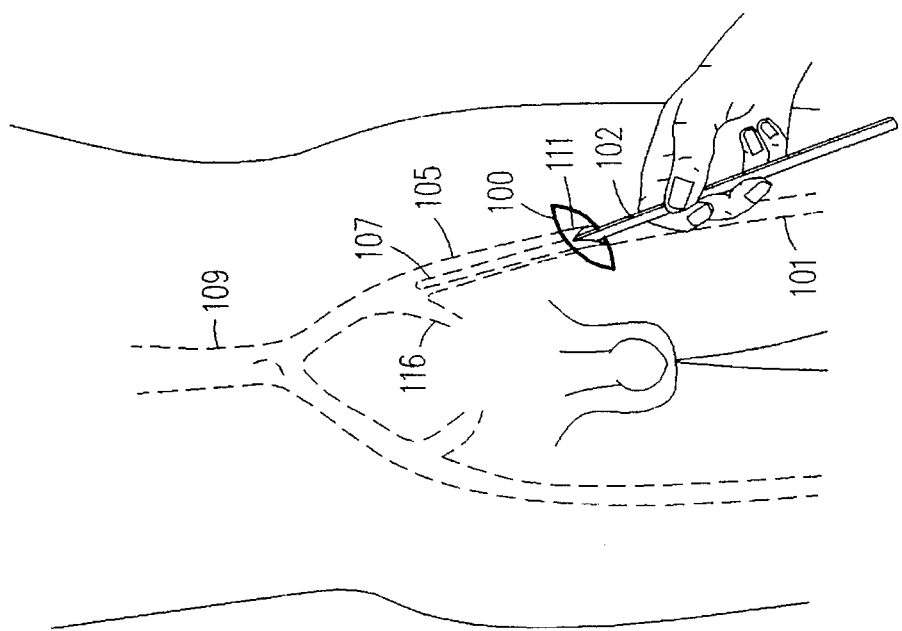

Referring to FIG. 3A, the surgeon makes incision 100 near the patient's groin and into femoral artery 101 and advances guide probe 102 through the femoral artery to the external iliac artery 105, and more particularly to stenosed region 107 below aorta 109. It should be appreciated that a "variform" intraluminal member of the type disclosed in co-pending and commonly invented U.S. patent application Ser. No. 08/287,580, filed Aug. 9, 1994 allowed may be utilized as an intraluminal guide. FIG. 3B depicts the surgeon pushing blunt distal tip 27 of spiral member 20 around femoral artery 101 and into plane 111 that comprises connective tissues 115 between the artery and surrounding muscles 117 (see FIG. 3C). Artery 101 is positioned in spiral gap 35 at the distal end of the spiral member 20. As can be seen in FIG. 3A, the distal portion "DP" of spiral member 20 may flex significantly relative to proximal portion "PP" along the flexible portion "FP" allowing the surgeon to substantially bend distal tip 27 to first engage artery 101 in spiral gap 35.

Figure 3C:
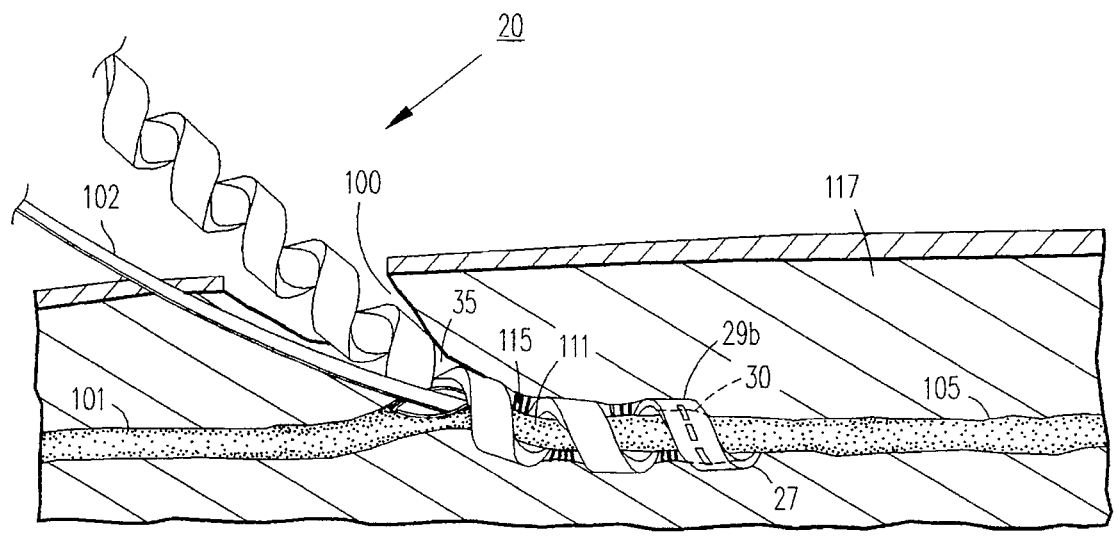
Figure 3D:
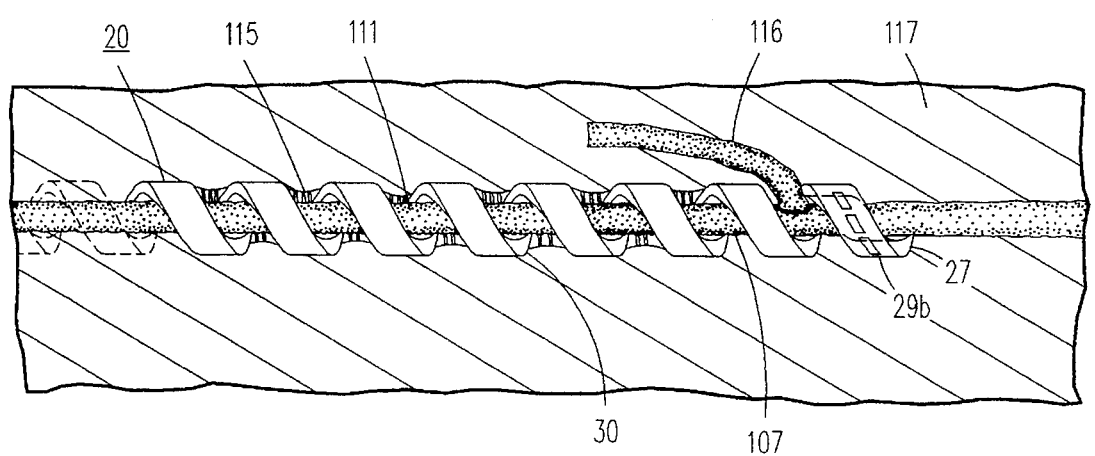

As shown in FIGS. 3B–3C, the surgeon then advances the constraint helically and distally thus "corkscrewing" the device around artery 101 and capturing the artery in bore 30 of the constraint. As shown in FIG. 3C, when spiral member 20 is advanced in plane 111 around the artery, blunt tip 27 bluntly dissects connective tissues 115 and may also dissect around branch artery 116. The spiral member acts as a screw to advance itself distally in plane 111 with guide probe 102 acting as a guide. FIG. 3D illustrates iliac artery 105 captured within bore 30 of spiral member 20. An imaging technology (e.g., x-ray) is utilized to view the constraint, and more particularly radiopaque marks 29a and 29b, as it is advanced to a suitable location. After placement around stenosed region 107, the surgeon withdraws guide probe 102.

Thereafter, as shown in FIG. 3E, the surgeon advances working end 119 of transluminal dilation-type catheter 120 to stenosed region 107 of iliac artery 105. FIG. 3F illustrates balloon member 122 in an expanded state with balloon walls 125 pressing occlusion 127 and vessel wall 130 against inner surface "IP" of the constraint along its interior bore 30, thus compacting the occlusion. The radial dimension "RD" of the constraint is thick enough to resist torsional deformation of the constraint that would result in enlargement of interior bore 30. The endovascular treatment is viewed contemporaneously with an imaging technology to assess the compaction of the occlusion.

As can be seen in FIG. 3F, expansion of balloon member 122 may tend to bulge vessel wall 130 radially outward in the spiral gaps between convolutions of the constraint lessening the compaction of the occlusion in the locations of the spiral gaps. Therefore, the surgeon may move the constraint axially and re-expand balloon member 122 to compact other portions of occlusion 127 (not shown). It should be appreciated that spiral member 20 may have a variable spiral lead as disclosed in Ser. No. 08/367,755, docket no. KP-41111, now U. S. Pat. No. 5,505,299 referenced above, for dissecting tissues in 360° degrees around the artery to allow the surgeon to slide the constraint axially over the artery instead of unscrewing the constraint.

It should be appreciated that the exemplary method of using an extraluminal constraint to limit the expansion of the transverse dimension of a vessel may be utilized with an atherectomy-type catheter to cut away portions of occlusion 127 (compare FIG. 3E). Also, the above-described procedure may be utilized when an endovascular graft or stent (not shown) is placed in a stenosed region of a vessel to prevent over-expansion of a vessel wall. It should also be appreciated that an extraluminal constraint may be made of biocompatible or bioabsorbable material for temporary or permanent implantation around an anatomic structure in a body, for example to cooperate with an intraluminal stent or graft.

It should be appreciated that constraint 20 may be adapted for introduction and placement through a trocar sleeve into an endoscopic or insufflated workspace for constraining an anatomic vessel. In such a method of use, the surgeon may grasp constraint 20 with a conventional elongate grasper or the constraint may be coupled to an elongate semi-rigid introducer member.

From the foregoing, it can be seen that extraluminal constraints and methods are provided for constraining a transverse dimension of an anatomic structure to facilitate an intraluminal treatment in a minimally invasive procedure or in an open procedure. It can be readily seen that extraluminal constraints may be manufactured in various special sizes and embodiments for constraining various anatomic structures having a lumen to facilitate an intraluminal treatment, e.g., veins, arteries, ureter, colon, bile ducts, pancreatic ducts or hepatic ducts, esophagus, etc. It should be appreciated that the bore diameter (and associated spiral lead dimension) may range from less than 0.1 inches to more than 2.0 inches for different diameter constraints.

This disclosure is illustrative and not limiting. Although specific features of the invention are shown in some drawings and not in others, this is for convenience only and any feature may be combined with another in accordance with the invention and are intended to fall within the scope of the appended claims.

What is claimed is:

1. A method of intraluminally treating an anatomic vessel, comprising the steps of:

introducing a helically shaped vessel-constraining structure into an interior of a body to a position proximate to an exterior of a vessel wall around a diseased portion of said anatomic vessel;

positioning said vessel-constraining structure substantially around said diseased portion thereby constraining a transverse dimension of said diseased portion;

advancing a working end of a transluminal catheter to said diseased portion; and treating said diseased portion intraluminally with said working end of said transluminal catheter.

2. The method of claim 1, wherein said vessel-constraining structure comprises a spiral member defining a spiral gap and an interior bore, the positioning step including the steps of:

disposing said diseased portion in said spiral gap; and helically and distally advancing said spiral member thereby positioning said diseased portion in said interior bore.

3. The method of claim 2, contemporaneous with the helically advancing step, the step of bluntly dissecting connective tissues in a plane around the exterior of the vessel wall with a blunt distal tip of the spiral member.

4. The method of claim 1, the positioning step including the step of contemporaneously viewing the positioning of the constraint with an imaging technology to insure the constraint is positioned in a particular location.

5. The method of claim 1, wherein the treating step includes treating said diseased portion with a dilation-type catheter.

6. The method of claim 5, wherein the treating step includes the step of compacting an occlusion within said diseased portion by pressing said occlusion between an expansion portion of said dilation catheter and said vessel-constraining structure.

7. The method of claim 1, wherein the treating step includes treating said diseased portion with an atherectomy-type catheter.

8. The method of claim 1, wherein the treating step includes treating said diseased portion with a placement of an intraluminal graft.

9. The method of claim 1, wherein the treating step includes treating said diseased portion with a placement of an intraluminal stent.

* * * * *